United States Patent
Pfefferle et al.

(10) Patent No.: US 6,960,211 B1
(45) Date of Patent: Nov. 1, 2005

(54) OSTEOSYNTHETIC BONE PLATE

(75) Inventors: Joachim Pfefferle, Munstertal (DE);
Ulrich Joos, Munster (DE)

(73) Assignee: Medartis AG, Basel (CH)

( * ) Notice: Subject to any disclaimer, the term of this patent is extended or adjusted under 35 U.S.C. 154(b) by 0 days.

(21) Appl. No.: 09/979,252

(22) PCT Filed: May 25, 2000

(86) PCT No.: PCT/CH00/00299

§ 371 (c)(1),
(2), (4) Date: Nov. 21, 2001

(87) PCT Pub. No.: WO00/71031

PCT Pub. Date: Nov. 30, 2000

(30) Foreign Application Priority Data

May 25, 1999 (DE) ............................ 299 09 025 U

(51) Int. Cl.[7] ............................ A61B 17/56; A61F 2/30
(52) U.S. Cl. .................................................. 606/69
(58) Field of Search ........................... 606/61, 69, 70, 606/71

(56) References Cited

U.S. PATENT DOCUMENTS

| | | | | |
|---|---|---|---|---|
| 4,800,874 A | * | 1/1989 | David et al. .................. | 128/92 |
| 4,905,679 A | | 3/1990 | Morgan | |
| 5,487,741 A | * | 1/1996 | Maruyama et al. ........... | 606/60 |
| 5,616,144 A | * | 4/1997 | Yapp et al. .................... | 606/61 |
| 5,690,631 A | | 11/1997 | Duncan et al. | |
| 5,718,705 A | * | 2/1998 | Sammarco .................... | 606/69 |
| 5,954,722 A | * | 9/1999 | Bono ........................... | 606/61 |
| 6,129,730 A | * | 10/2000 | Bono et al. ................... | 606/73 |
| 6,306,136 B1 | * | 10/2001 | Baccelli ....................... | 606/61 |
| 6,458,133 B1 | * | 10/2002 | Lin ............................. | 606/69 |
| 6,506,191 B1 | * | 1/2003 | Joos ............................ | 606/72 |
| 6,730,091 B1 | * | 5/2004 | Pfefferle et al. .............. | 606/70 |
| 2002/0045901 A1 | * | 4/2002 | Wagner et al. ................ | 606/69 |

FOREIGN PATENT DOCUMENTS

| | | |
|---|---|---|
| DE | 2340880 | 4/1975 |
| EP | 433852 | 6/1991 |
| WO | WO 98/44849 | 10/1998 |

* cited by examiner

*Primary Examiner*—Kevin Shaver
*Assistant Examiner*—Anuradha Ramana
(74) *Attorney, Agent, or Firm*—Leydig, Voit & Mayer, Ltd.

(57) ABSTRACT

An osteosynthetic bone plate has elongated compression cavities containing eccentric countersinks. The plate includes a longitudinal axis, a transverse axis, a plate upper side, and a plate lower side for facing bone fragments. The bone plate also includes a compression element with two plate braces which run substantially parallel to the longitudinal axis. Both plate braces are linked together by bridging struts which intersect the longitudinal axis. A plate brace has an eyelet on at least one of the outer sides of the compression element. Additional eyelets can be positioned in front of this eyelet. A compression cavity is situated in each of said eyelets and a connecting strut, which intersects the transverse axis, extends between the eyelets which are located on each plate brace.

17 Claims, 4 Drawing Sheets

OSTEOSYNTHETIC BONE PLATE

BACKGROUND OF THE INVENTION

Osteosynthetic bone plates for the treatment of fractures, in particular for the reconstruction of mandibular fractures are fitted intraoperatively in order to fix bone fragments together. This may be necessary in osteosynthesis, following accidents in which a bone has shattered into bone fragments, or in orthognathic/maxillofacial treatment for surgical control of abnormal positioning after an osteotomy, and subsequent positional correction of the bone fragments.

Such a bone plate is used principally to span and fix two bone fragments together, one part of the bone plate in each case being connected releasably to a bone fragment. In order to establish the connection between the temporarily fitted bone plate and the bone fragments, the bone plate has through-holes for the insertion of bone screws which engage in the bone fragments. The bone plates should be able to bend in order to correctly match the bone geometry, but at the same time they must guarantee sufficient stability. These two requirements are in principle mutually contradictory. Moreover, the bone plates should permit the buildup of a pressure between the fragments, which is achieved by the opposite arrangement of what are referred to as compression holes.

DE 23 40 880 A1 discloses a solid linear bone plate which is used for treating jaw fractures and which, spanning the fracture site on the jaw bone, is screwed onto both of the bone fragments that are to be joined together. In each half of the bone plate there are two oblong holes oriented toward the plate center and toward the fracture site. On the side directed away from the jaw bone, the oblong holes have a countersink with a screw seat configured as a beveled plane surface. At least one oblong hole per half is inclined relative to the plate center. On the side directed toward the jaw bone, the bone plate has a projecting notched strut at the center. As a result of the arrangement of the oblong holes and the beveled screw seats, the bone fragments are compressed toward the fracture site when the inserted bone screws are tightened; the pressure thus built up between the fragments results in improved healing of the bone fracture.

However, because of it's rigidity, this plate cannot readily be adapted to the existing bone geometry. A rigid plate which cannot be sufficiently bent to fit the jaw bone has the effect that the bone fragment less anchored in the jaw is moved toward the plate, and dislocations therefore occur. Even slight shifts in the fracture area lead to the loss of the interfragment support, which results in greater mobility within the fracture area. The simple hole pattern on the plate additionally permits little variability in terms of attachment to the bone fragments. For example, in Prein, J. (editor): Manual of Internal Fixation in the Cranio-Facial Skeleton, Springer-Verlag Berlin 1998, page 30, straight or arcuate bone plates with compression holes for treating fractured mandibles are shown which have a thickness of 1.65 mm or 2.0 mm, respectively, and are designed for bone screws with an external thread diameter of 2.4 mm.

Thinner bone plates, for example with a thickness of between 0.5 mm and 0.9 mm, which can be bent more readily, are known in craniofacial applications (cf. Prein, loc. cit., page 28). Different configurations have been developed for this purpose, for example the L-plate, Y-plate, T-plate, H-plate, X-plate, double Y-plate or frame plate. Bone screws with an external thread diameter of 1.0 mm to 2.0 mm are used for these. However, these bone plates have no compression holes, but only simple cylindrical screw holes with countersinks for partially receiving the screw head. The provision of compression holes in these thinner plates has been avoided because opinion hitherto held that a greater plate thickness, for example 1.65 mm or 2.0 mm, was necessary for building up a pressure between the fragments. In addition, with the previously available production technology, it would have been extremely complicated to work compression holes into thinner bone plates, for example with the thickness of 1.0 mm.

According to the prior art hitherto disclosed, no bone plate has as yet been made available in which, even when absolutely correctly applied, sufficient stability for unimpeded bone healing is guaranteed and a pressure can be built up between the fragments for the dynamic compression for improved bone fracture healing. Particular requirements exist for example in respect of:

fractures of atrophic jaws;
unstable oblique fractures;
infected mandibular fractures;
unstable jaw angle fractures; and
mandibular fractures in noncooperative patients.

In view of the cited shortcomings of the bone plates known to date, the object of the invention is to make available a bone plate particularly for the treatment of mandibular fractures, which, as a result of greater deformability, can be readily bent to the respective contour of the bone fragments, but which nevertheless guarantees a secure and positionally stable fixation of the bone fragments. That is to say, the bone plate must be easily deformable on the one hand and yet must have adequate rigidity on the other. Moreover, the bone plate is to have compression holes in order to be able to generate a pressure between the fragments—in the sense of compression osteosynthesis—for promoting the bone healing. Furthermore, the bone plate to be produced must not pinch the nerve issuing at the mandible and, in the event of comminuted fractures, small bone fragments must also be able to be fixed individually on the bone plate. Finally, the bone plate must be able to be applied using conventional bone screws and must be able to be produced economically in series.

SUMMARY OF THE INVENTION

The osteosynthetic bone plate is used for the treatment of fractures, in particular for the reconstruction of mandibular fractures. The plate is intended to be screwed by means of conventional bone screws, which have screw heads, onto the bone fragments which are to be joined together in accordance with the principle of compression osteosynthesis at a fracture line. The plate has oblong compression holes with eccentric countersinks. A longitudinal axis and a transverse axis, and also a plate upper side and a plate lower side, the latter facing toward the bone fragments, can be defined on the plate. The bone plate comprises a compression part which has two plate braces extending at least substantially parallel to the longitudinal axis. The two plate braces are connected to one another by bridging struts which intersect the longitudinal axis. A plate brace has an eyelet at least on one of the outer flanks of the compression part. An eyelet is preferably arranged on both outer flanks. A compression hole is preferably situated in each of the eyelets, and a connecting strut which intersects the transverse axis extends between the eyelets located on each plate brace.

The following description refers to preferred illustrative embodiments of the bone plate according to the invention: The compression holes have, with their longitudinal extent, an orientation in the direction of the brace axis or assume an angle ≠0° in relation to the brace axis and have eccentric countersinks on the plate upper side. In a continuation of the compression part, attachment struts adjoin the eyelets and extend on the brace axes. A disk-shaped plate member is situated at the end of each of the attachment struts, and further plate members connected by attachment struts can be positioned in front of said plate member. A fixation hole for receiving a bone screw is in each case provided in the plate members.

The connecting struts between the eyelets have a greater width than the attachment struts leading to the plate members. The fixation holes' on the plate upper side have a countersink for receiving the heads of the bone screws in a partially recessed manner. Two bridging struts are preferably provided on the bone plate and extend symmetrically or asymmetrically with respect to the transverse axis. In the case of a symmetrical arrangement of the bridging struts, both bridging struts extend laterally from the outer flank of one eyelet on one brace axis to the outer flank of the opposite eyelet on the other brace axis. In the case of an asymmetric arrangement of the bridging struts, by contrast, one bridging strut is offset toward the transverse axis and, as seen from the latter, extends in front of the pair of eyelets which lie opposite each other on the two brace axes.

The bone plate has a material thickness in the range from 0.5 mm to 1.5 mm and is preferably made of titanium of quality grade 1 or grade 2. The bone screws inserted in the compression holes and in the fixation holes are provided for monocortical screwing to the bone fragments.

SPECIFIC DESCRIPTION OF THE INVENTION

In the following detailed description of illustrative embodiments of the osteosynthetic bone plate according to the invention, reference is made to the attached drawings.

Figure 1B:
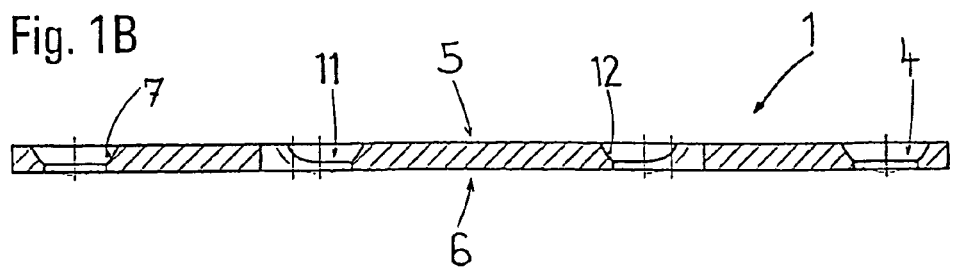
FIG. 1B shows the view according to FIG. 1A, in a cross section along the line A—A.
Figure 1A:
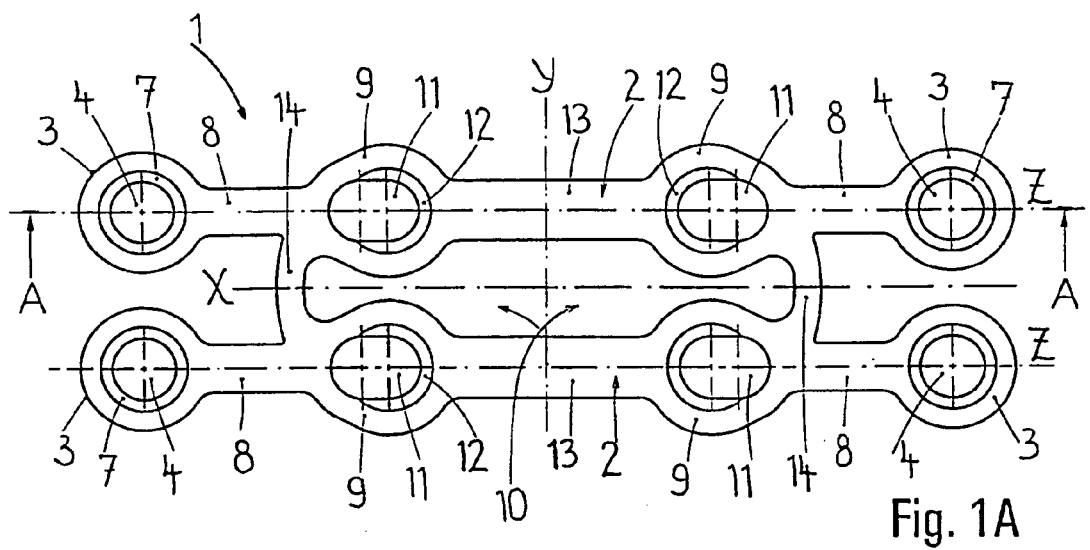
FIG. 1A shows a plan view of a symmetrical bone plate with 4 compression holes and 4 cylindrical fixation holes.

As illustrated in FIGS. 1A and 1B, the bone plate 1 constructed symmetrically in relation to the longitudinal axis X and the transverse axis Y has two plate braces 2 running parallel to the longitudinal axis X and spaced apart from one another. The plate braces 2 extend along the brace axes Z. Each plate brace 2 ends at the outside with a disk-shaped plate member 3, at the center of which a cylindrical fixation hole 4 is provided which, on the plate upper side 5, has a countersink 7 for receiving a screw head in a partially recessed manner. The fixation hole 4 opens out cylindrically on the plate lower side 6, which faces toward the bone fragments that are to be joined. From the plate members 3, an attachment strut 8 extends along each of the brace axes Z toward the transverse axis Y.

The four attachment struts 8 each adjoin an eyelet 9 of the compression part 10 of the bone plate 1. Provided in each eyelet 9 there is an oblong compression hole 11 of conventional contour whose longitudinal extent lies on the brace axis Z. Toward the transverse axis Y, the individual compression hole 11 has, on the plate upper side 5, a countersink 12 which runs out harmonically in the compression hole 11 increasingly away from the transverse axis Y. Thus, a bone screw fitted as it were eccentrically in the compression hole 11 is pressed in a known manner toward the transverse axis Y with its head penetrating into the compression hole 11 and in so doing entrains the screwed-on bone fragment with it. If the bone screws are positioned symmetrically to the transverse axis Y, the bone fragments which are to be joined together are pressed on each other in the sense of compression osteosynthesis.

Extending between the eyelets 9 on both sides of the transverse axis Y on a plate brace 2 there is a connecting strut 13 which runs on the brace axis Z and connects the two eyelets 9 to each other. Compared to the attachment struts 8, the connecting struts 13 have a greater width and for this reason they also have a higher degree of rigidity. The two plate braces 2 are connected to one another by two bridging struts 14 symmetrical to the transverse axis Y. The bridging struts 14 each extend laterally from the junction of the attachment strut 8 with one eyelet 9 on one brace axis Z to the junction of the attachment strut 8 with the opposite eyelet 9 on the other brace axis Z. As the bone plate 1, with a thickness of for example 1.0 mm, is made of titanium of quality grade 1 or grade 2 with two plate braces 2 and the bridging struts 14, the bone plate 1 can be bent to correctly match the respective geometry of the bone fragments and it also has sufficient rigidity for positionally stable fixation of the bone fragments.

Figure 2:
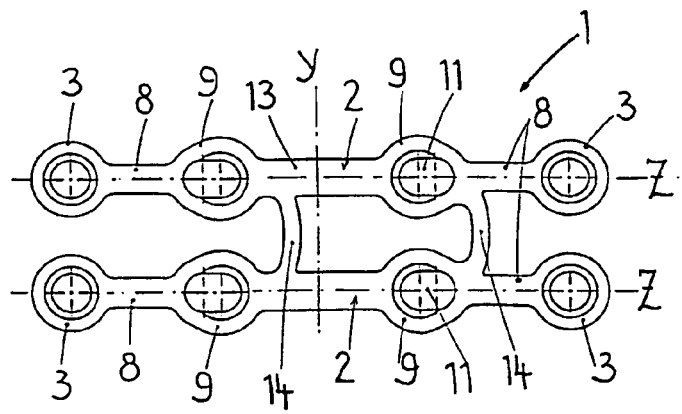
FIG. 2 shows a plan view of an asymmetrical bone plate with 4 compression holes and 4 cylindrical fixation holes.

Referring to FIG. 2, the difference from bone plate 1 in FIG. 1, is that in the bone plate 1 shown in FIG. 2 the bridging struts 14 connecting the two plate braces 2 are arranged asymmetrically with respect to the transverse axis Y. The right bridging strut 14 again extends laterally from the junction of the attachment strut 8 with an eyelet 9 on one brace axis Z to the junction of the attachment strut 8 with the opposite eyelet 9 on the other brace axis Z. By contrast, the left bridging strut 14 is offset toward the Y axis; this bridging strut 14 extends laterally from in front of the junction of the connecting strut 13 with one eyelet 9 on one brace axis Z to a position in front of the junction of the connecting strut 13 with the opposite eyelet 9 on the other brace axis Z. A bone plate 1 configured in this way is primarily of use for application to a paramedian fracture of the mandible, where the issuing nerve must not be pressed by a plate part (see description of FIG. 7B).

Figure 3:
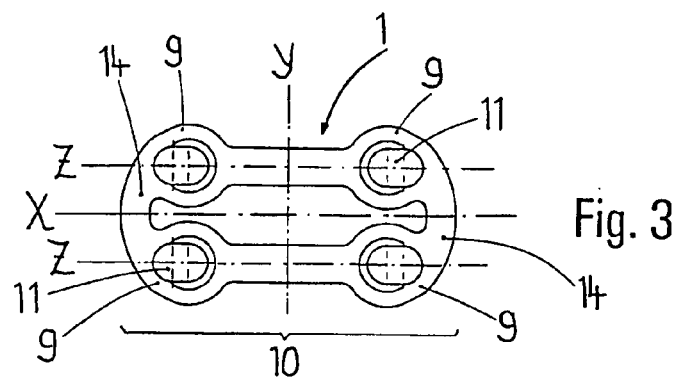
FIG. 3 shows a plan view of a symmetrical bone plate with 4 compression holes.

In the simplified bone plate 1 shown in FIG. 3, only the compression part 10 is provided. The outwardly directed attachment struts 8 and the plate members 3 at the very outer ends with the fixation holes 4 are not present here. As in the embodiment according to FIG. 1, the bridging struts 14 in principle extend from the outer flank of one eyelet 9 on one brace axis Z to the outer flank of the opposite eyelet 9 on the other brace axis Z. An illustrative application of this bone plate 1 is described with reference to FIG. 6A.

Figure 4:
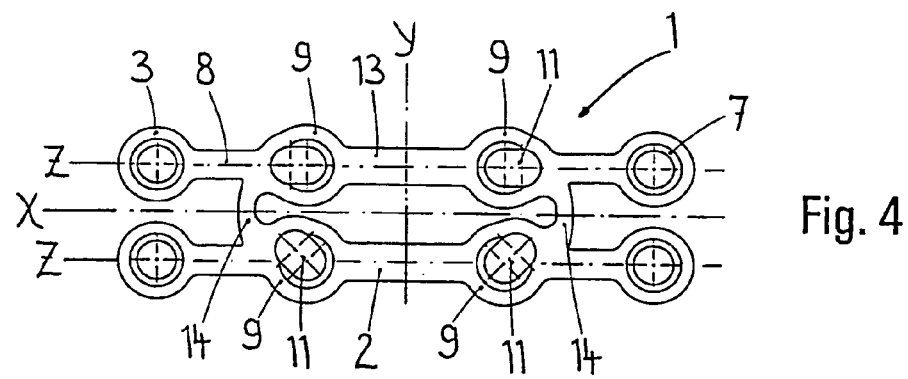
FIG. 4 shows a plan view of a symmetrical bone plate according to FIG. 1A with 2 compression holes oriented at an angle to the longitudinal axis.

The particular feature of the symmetrical embodiment illustrated in FIG. 4 compared to the basic embodiment according to FIG. 1 is that the two oblong compression holes 11 with the eyelets 9 on the lower plate brace 2 do not extend longitudinally on the brace axis Z or parallel to the longitudinal axis X, but assume the angle α. This is useful in cases where, in a special fracture pattern, a pressure between the fragments is to be built up extending obliquely from the lower plate brace 2 to the longitudinal axis X.

Figure 5A:
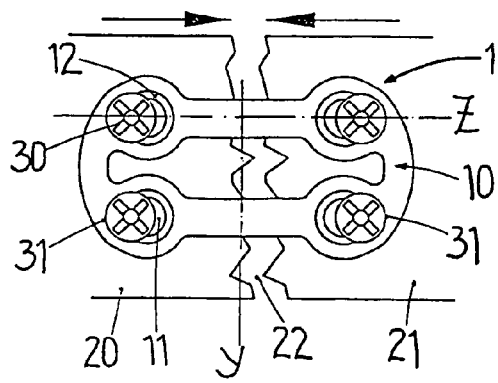
FIG. 5A shows the symmetrical bone plate according to FIG. 3 at the start of compression osteosynthesis with an open bone fracture.
Figure 5B:
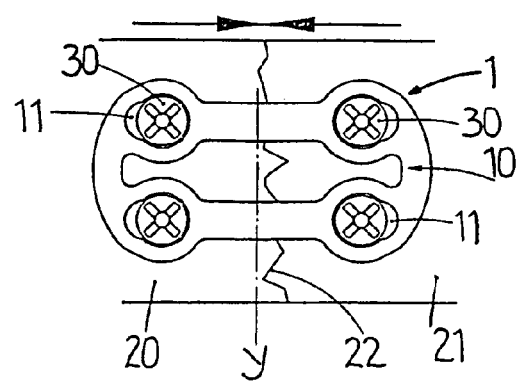
FIG. 5B shows the view according to FIG. 5A during compression osteosynthesis with a closed bone fracture.

FIGS. 5A and 5B illustrate the principle of compression osteosynthesis using a bone plate 1 according to FIG. 3 by way of example.

In the starting situation (see FIG. 5A), the fracture line 22 to be closed is present between the two bone fragments 20, 21 to be joined, and the bone plate 1 is to be placed with its compression part 10 across this line. The bone plate 1 is of the type referred to as mini plates. The bone screws 30 are introduced into the oblong compression holes 11, directed away from the countersinks 12, i.e. at the greatest possible distance from one another as viewed on the respective plate brace 2 and the associated brace axis Z. As can be seen, the screw heads 31 of the bone screws 30 are screwed preferably monocortically into the bone fragments, i.e. farther away from the fracture line 22 and the transverse axis Y.

FIG. 5B shows that, as the bone screws 30 are screwed farther into the bone fragments 20, 21, the screw heads 31 come to lie in the countersinks 12 —as a result of the specially contoured countersinks 12 in the compression holes 11. The bone fragments 20, 21 hanging on the bone screws 30 are entrained in the direction of the transverse axis Y and the fracture line 22 until finally the fracture line 22 is closed and the bone fragments 20, 21 are joined together with compression.

FIGS. 6A to 7B illustrate examples of some applications of different embodiments of the bone plate 1 according to the invention in mandibular fractures.

Figure 6A:
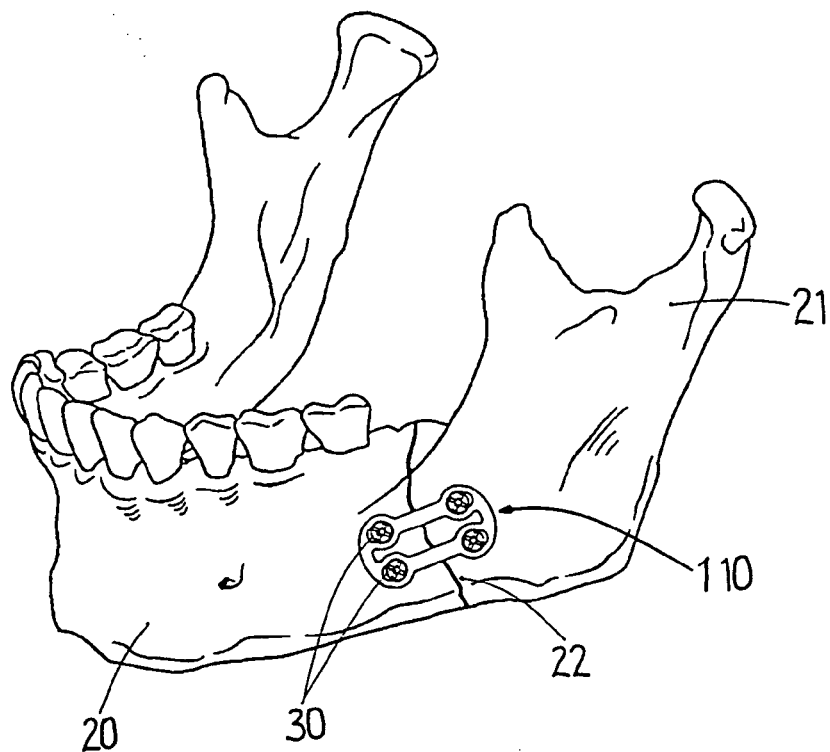
FIG. 6A shows the symmetrical bone plate according to FIG. 3 fitted laterally on the mandible with a jaw angle fracture.

In FIG. 6A, a jaw angle fracture is treated with a bone plate 1 in the configuration according to FIG. 3, which only has the compression part 10. The bone plate 1 fixed with four bone screws 30 spans the fracture line 22 and connects as bone fragments 20, 21 the body of the mandible and the ramus of the mandible.

Figure 6B:
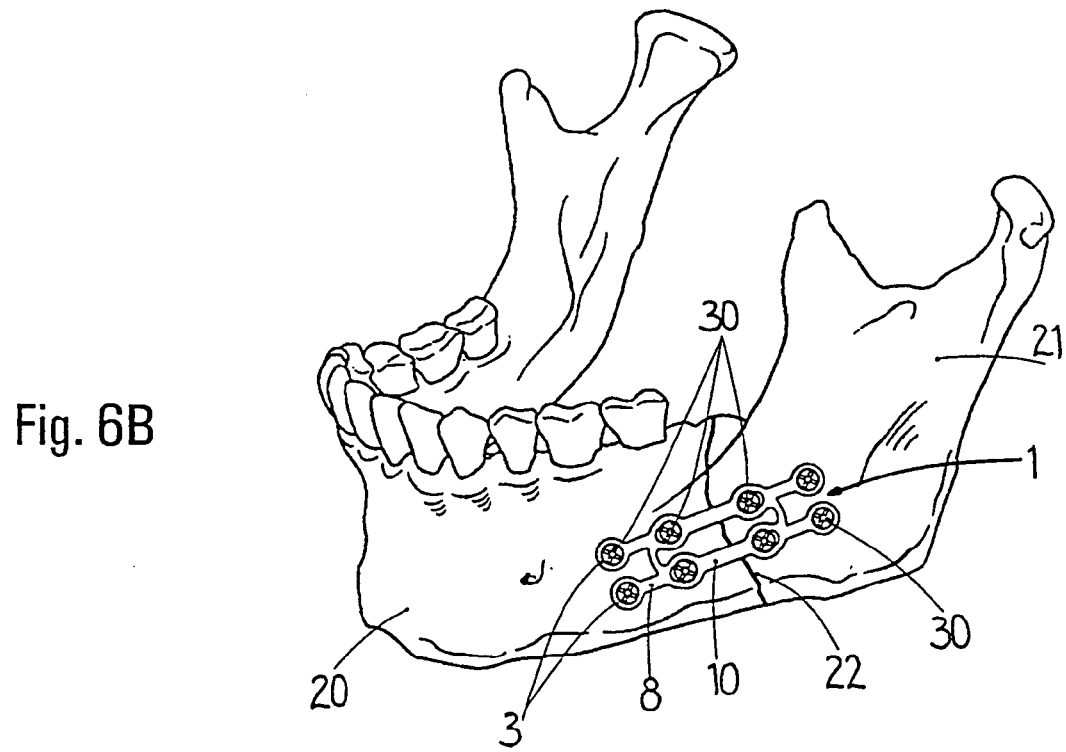
FIG. 6B shows the symmetrical bone plate according to FIG. 1A fitted laterally on the mandible with a jaw angle fracture.

In FIG. 6B, a jaw angle fracture is likewise treated with a symmetrical bone plate 1 in the configuration according to FIG. 1 which comprises the compression part 10 and the attachment struts 8 extending beyond this and the outer plate members 3. The body of the mandible and the ramus of the mandible are once again connected as bone fragments 20, 21 across the fracture line 22. In addition to the four bone screws 30 in the compression part 10, the bone fragments 20, 21 are secured with in each case two bone screws 30 inserted in the outer plate members 3.

Figure 7A:
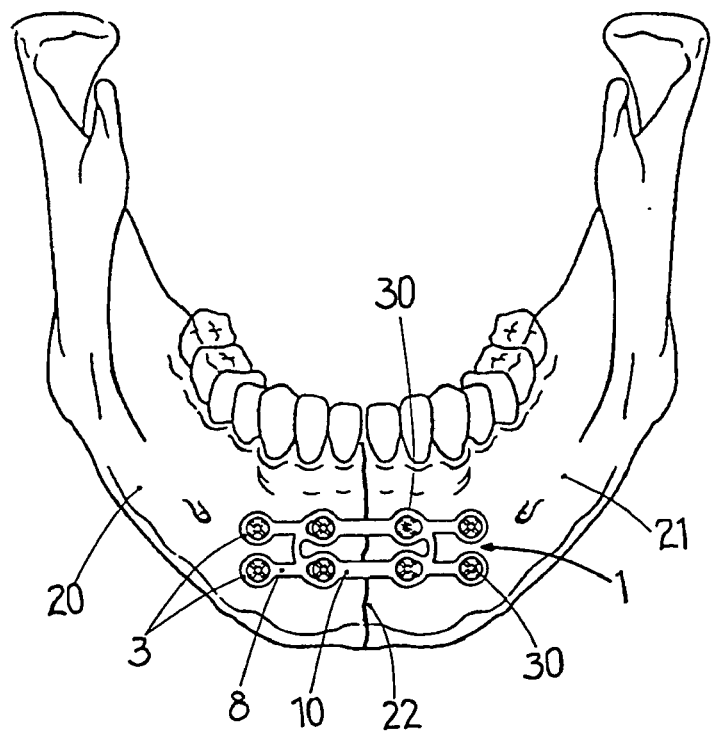
FIG. 7A shows the symmetrical bone plate according to FIG. 1A fitted frontally on the mandible with a median fracture.

In FIG. 7A, a median fracture of the mandible is treated likewise with a symmetrical bone plate 1 in the configuration according to FIG. 1, which comprises the compression part 10 and the attachment struts 8 extending beyond this and the outer plate members 3. Two parts of the broken body of the mandible as bone fragments 20, 21 are connected to one another across the median fracture line 22. Here once again, in addition to the four bone screws 30 in the compression part 10, the bone fragments 20, 21 are fixed in a positionally stable manner with the two bone screws 30 inserted in the outer plate members 3.

Figure 7B:
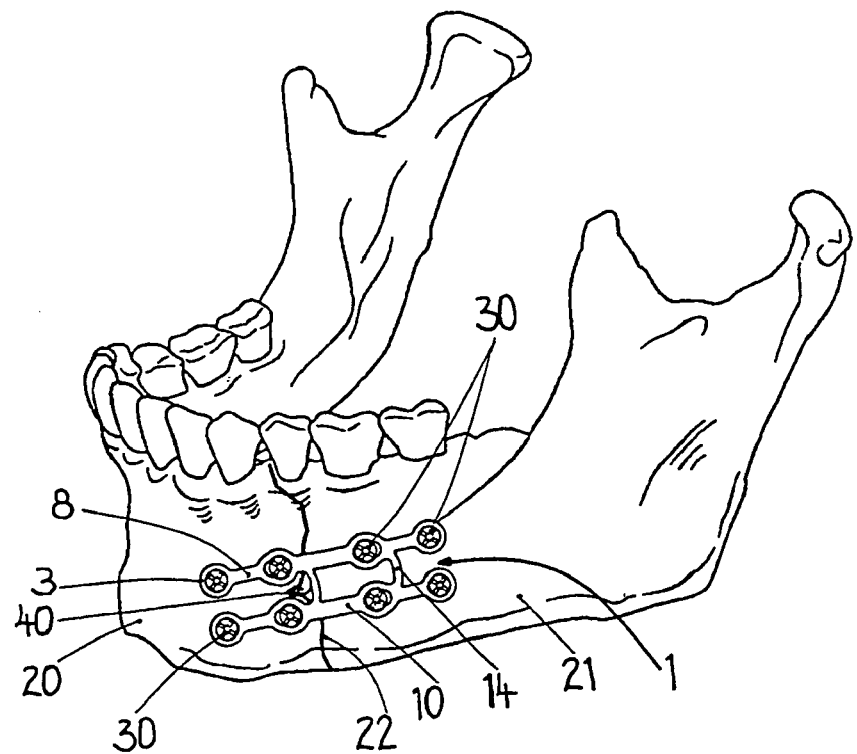
FIG. 7B shows the asymmetrical bone plate according to FIG. 2 fitted laterally on the mandible with a paramedian fracture.

In FIG. 7B, an asymmetrical bone plate 1 in the configuration according to FIG. 2 is used for the illustrated treatment of a paramedian fracture of the mandible. This bone plate 1 consists of the compression part 10, the attachment struts 8 extending beyond the latter, the outer plate members 3, and the asymmetrically arranged bridging struts 14 between the two plate braces 2. The bone plate 1 is used to connect, as bone fragments 20, 21, two parts of the eccentrically broken body of the mandible across the paramedian fracture line 22. The emergent nerve 40 (mental foramen) lies free and is not pinched by any of the plate parts. The bone fragments 20, 21 are secured in each case by four bone screws 30 in total.

What is claimed is:

1. An osteosynthetic bone plate for osteosynthetic compression of bone fragments for the reconstruction of mandibular fractures, the bone plate having a longitudinal axis and a transverse axis and comprising:
    a plate upper side and a plate lower side for facing toward the bone fragments;
    a compression part which has two plate braces extending at least substantially parallel to the longitudinal axis;
    bridging struts, which intersect the longitudinal axis, connecting the two plate braces to one another, each plate brace extending along a brace axis and having an eyelet on at least one outer flank of the compression part;
    attachment struts adjoining the eyelets and extending along the brace axis;
    a disk-shaped plate member situated at an end of each of the attachment struts and having a fixation hole for receiving a bone screw, each fixation hole having a countersink on the plate upper side for receiving the head of a bone screw in a partially recessed manner;
    connecting struts having a greater width than the attachment struts, which intersect the transverse axis, and extend between the eyelets located on each plate brace; and
    oblong compression holes having a longitudinal axis extending longitudinally along the brace axis, and eccentric countersinks on the plate upper side for the compression of the bone fragments, one of the compression holes being situated in each of the eyelets, wherein the bone plate has a thickness in the range from 0.5 mm to 1.5 mm.

2. The osteosynthetic bone plate as claimed in claim 1, wherein two bridging struts extend symmetrically or asymmetrically with respect to the transverse axis.

3. The osteosynthetic bone plate as claimed in claim 2, wherein in
    a symmetrical arrangement of the bridging struts, the two bridging struts extend laterally from an outer flank of one eyelet on one plate brace to an outer flank of an opposite eyelet on the other plate brace, or
    in an asymmetric arrangement of the bridging struts, one bridging strut is offset toward the transverse axis and extends from in front of one eyelet on one plate brace to in front of the opposite eyelet on the other plate brace.

4. The osteosynthetic bone plate as claimed in claim 1, wherein the bone plate is made of titanium.

5. The osteosynthetic bone plate as claimed in claim 1 wherein bone screws inserted in the compression holes and in the fixation holes provide monocortical engagement of the bone fragments.

6. An osteosynthetic bone plate for osteosynthetic compression of bone fragments for the reconstruction of mandibular fractures, the bone plate having a longitudinal axis and a transverse axis and comprising:
   a plate upper side and a plate lower side for facing toward the bone fragments;
   a compression part which has two plate braces extending at least substantially parallel to the longitudinal axis;
   bridging struts, which intersect the longitudinal axis, connecting the two plate braces to one another, each plate brace extending along a brace axis and having an eyelet on at least one outer flank of the compression part;
   connecting struts, which intersect the transverse axis, and extend between the eyelets located on each plate brace; and
   oblong compression holes having a longitudinal axis extending longitudinally at an angle ≠0° in relation to the brace axis and eccentric countersinks on the plate upper side for the compression of the bone fragments, one of the compression holes being situated in each of the eyelets, wherein the bone plate has a thickness in the range from 0.5 mm to 1.5 mm.

7. The osteosynthetic bone plate as claimed in claim 6, further comprising:
   attachment struts adjoining the eyelets and extending along the brace axis; and
   a disk-shaped plate member situated at an end of each of the attachment struts and having a fixation hole for receiving a bone screw.

8. The osteosynthetic bone plate as claimed in claim 7, wherein the connecting struts have a greater width than the attachment struts and the fixation holes have a countersink on the plate upper side for receiving the heads of the bone screws in a partially recessed manner.

9. The osteosynthetic bone plate as claimed in claim 6, wherein two bridging struts extend symmetrically or asymmetrically with respect to the transverse axis.

10. The osteosynthetic bone plate as claimed in claim 9, wherein in
    a symmetrical arrangement of the bridging struts, the two bridging struts extend laterally from an outer flank of one eyelet on one plate brace to an outer flank of an opposite eyelet on the other plate brace, or
    in an asymmetric arrangement of the bridging struts, one bridging strut is offset toward the transverse axis and extends from in front of one eyelet on one plate brace to in front of the opposite eyelet on the other plate brace.

11. The osteosynthetic bone plate as claimed in claim 6, wherein the bone plate is made of titanium.

12. The osteosynthetic bone plate as claimed in claim 6 wherein bone screws inserted in the compression holes and in the fixation holes provide monocortical engagement of the bone fragments.

13. An osteosynthetic bone plate for osteosynthetic compression of bone fragments for the reconstruction of mandibular fractures, the bone plate having a longitudinal axis and a transverse axis and comprising:
    a plate upper side and a plate lower side for facing toward the bone fragments;
    a compression part which has two plate braces extending at least substantially parallel to the longitudinal axis;
    bridging struts, which intersect the longitudinal axis, connecting the two plate braces to one another, each plate brace extending along a brace axis and having an eyelet on at least one outer flank of the compression part;
    attachment struts adjoining the eyelets and extending along the brace axis;
    a disk-shaped plate member situated at an end of each of the attachment struts and including a fixation hole having a countersink on the plate upper side for receiving the head of a bone screw in a partially recessed manner;
    connecting struts, which intersect the transverse axis, and extend between the eyelets located on each plate brace and have a greater width than the attachment struts; and
    oblong compression holes having a longitudinal axis extending longitudinally along the brace axis, or extending longitudinally at an angle ≠0° in relation to the brace axis and eccentric countersinks on the plate upper side for the compression of the bone fragments, one of the compression holes being situated in each of the eyelets, wherein the bone plate has a thickness in the range from 0.5 mm to 1.5 mm.

14. The osteosynthetic bone plate as claimed in claim 13 wherein two bridging struts extend symmetrically or asymmetrically with respect to the transverse axis.

15. The osteosynthetic bone plate as claimed in claim 14, wherein in
    a symmetrical arrangement of the bridging struts, the two bridging struts extend laterally from an outer flank of one eyelet on one plate brace to an outer flank of an opposite eyelet on the other plate brace, or
    in an asymmetric arrangement of the bridging struts, one bridging strut is offset toward the transverse axis and extends from in front of one eyelet on one plate brace to in front of the opposite eyelet on the other plate brace.

16. The osteosynthetic bone plate as claimed in claim 13, wherein the bone plate is made of titanium.

17. The osteosynthetic bone plate as claimed in claim 13 wherein bone screws inserted in the compression holes and in the fixation holes provide monocortical engagement of the bone fragments.

* * * * *